United States Patent [19]
Nishio et al.

[11] Patent Number: 5,092,334
[45] Date of Patent: Mar. 3, 1992

[54] NONCONTACT TYPE TONOMETER

[75] Inventors: Kouji Nishio; Yoshihiko Hanamura, both of Tokyo, Japan

[73] Assignee: Tokyo Kogaku Kikai Kabushiki Kaisha, Tokyo, Japan

[21] Appl. No.: 325,944

[22] Filed: Jun. 29, 1988

[30] Foreign Application Priority Data

Jun. 30, 1987 [JP] Japan .................. 62-163678
Jun. 30, 1987 [JP] Japan .................. 62-163679

[51] Int. Cl.$^5$ .............................. A61B 3/16
[52] U.S. Cl. .................................. 128/648
[58] Field of Search ............... 128/645, 648, 652

[56] References Cited

U.S. PATENT DOCUMENTS

| | | | |
|---|---|---|---|
| 3,572,100 | 3/1971 | Grolman | 128/645 |
| 4,799,489 | 1/1989 | Hideshima | 128/648 |
| 4,817,620 | 4/1989 | Katsuragi et al. | 128/652 |

*Primary Examiner*—Kyle L. Howell
*Assistant Examiner*—John Hanley
*Attorney, Agent, or Firm*—Fleit, Jacobson, Cohn, Price, Holman & Stern

[57] ABSTRACT

A noncontact type tonometer projects a fluid toward an eye-to-be-tested and obtains a measured value of eye pressure from a relation between transfigurations of the eye due to the fluid projection and the pressure projecting of the fluid. A detecting circuit senses a pulse wave of the person-to-be-tested and a calculating circuit determines at least one of the maximum eye pressure value, minimum eye pressure value and average pressure value of the eye dependent on the maximum fluctuation width of the detected pulse wave, a fluctuating quantity of the detected pulse wave, and the measured eye pressure value. The calculation circuit determines the pulse wave fluctuating quantity at the time point when the eye pressure is measured. The pulse wave of the person may be measured at a position remote from the eye. The tonometer may also include a display for displaying the pulse wave and a display controller for displaying the time point when the eye pressure is measured. The displayed eye pressure overlaps the displayed pulse wave to illustrate the relation between the measured eye pressure value and the pulse wave fluctuation.

3 Claims, 3 Drawing Sheets

NONCONTACT TYPE TONOMETER

INDUSTRIAL FIELD

This invention relates to a noncontact type tonometer for increasing the reliability on a result of the measurement of an eye pressure while taking into consideration the fluctuation of the eye pressure based on pulse fluctuation.

PRIOR ART

As a conventional tonometer, there is known a noncontact type tonometer, e.g., an air puff type tonometer, in which a fluid pulse is discharged toward an eye of a person-to-be-tested and the pressure value of the eye-to-be-tested is measured with reference to a relation between the transfiguration of the cornea of the eye-to-be-tested and the pressure of the pulse of the discharged fluid. In this type of a tonometer, an air pulse as a fluid pulse is discharged toward the eye-to-be-tested in a moment, e.g., in such a short period of time as several times of ten ms and the cornea is transfigured (e.g., applanation) in such a very short time as several ms in order to measure the eye pressure. By the way, the eye pressure of an eye-to-be-tested is fluctuated in response to the fluctuation of the pulse. The eye pressure is fluctuated at several mmHg maximum. Whereas, the eye pressure value of a normal eye of a man is normally 10 mmHg to 20 mmHg. Similarly, his pulse fluctuation is normally 60 to 120 times per minute (1 to 2 times per sec.) and the cycle of the pulse fluctuation is approximately 500 ms at the shortest. Therefore, when the eye pressure is measured without taking into consideration the eye pressure fluctuation caused by the pulse fluctuation at all, if, for example, the eye pressure measurement is carried out at the hill top of the pulse wave, the eye pressure value which is to be obtained becomes higher correspondingly thereto. On the contrary, if the eye pressure measurement is carried out in the valley of the pulse wave, the eye pressure value which is to be obtained becomes lower corresponding thereto. Therefore, if the eye pressure fluctuation caused by the pulse fluctuation is not taken into consideration, the reliability of such measured eye pressure value itself becomes low.

Accordingly, there has been proposed a tonometer for measuring an eye pressure taking into consideration the eye pressure fluctuation caused by the pulse fluctuation (see Japanese Patent Publication No. Sho 49-17476). In the tonometer disclosed in this Japanese Patent Publication No. Sho 49-17476, an eye pressure measurement is carried out in synchronism with the same phase place of the pulse wave caused by the pulse fluctuation. According to this tonometer, errors of measurement caused by the pulse fluctuation can be removed.

However, in a noncontact type tonometer, a strictness is required in alignment of the tonometer with respect to an eye-to-be-tested. In order to carry out the eye pressure measurement accurately, a sstrict aligning accuracy is required with regard to, for example, the position of the nozzle in the vertical and horizontal directions and the so-called working distance from the eye-to-be-tested to the tip of the nozzle. The degree of the alignment accuracy is so strict that the error from the correct aligning position must be a fragment or less of 1 mm. Therefore, in the tonometer disclosed in the Japanese Patent Publication No. Sho 49-17476, since the eye pressure measurement is carried out in synchronism with the same phase place of the pulse wave caused by the pulse fluctuation 1 to 2 times per second, the aligning state of the tonometer must be maintained for approximately 1 second maximum with respect to the eye-to-be-tested. However, since the eye-to-be-tested repeats a gazing flick or tremor at the cycle of 0.2 to 3 seconds within the range of a width from a fragile of 1 mm to 1 mm, it is difficult to maintain the aligning state for a period of 1 second. Therefore, the inspector or examiner needs a long experience. In addition, the operation of this type of conventional tonometer is troublesome.

SUMMARY OF THE INVENTION

The object of the present invention is to overcome the above-mentioned problem. This object can be achieved by providing a noncontact type tonometer comprising a pulse wave detecting means for detecting a pulse wave of a person-to-be-tested, a displaying means for displaying the pulse wave form detected by the pulse wave detecting means, and an overlap. display controlling means for displaying the time point when the measurement of the eye pressure is carried out in such a manner as to overlap with the pulse wave form displayed by the displaying means.

According to the above-mentioned constitution of the invention, the pulse wave of the person-to-be-tested is displayed on the displaying means, and the time point when the measurement of the eye pressure is carried out is displayed in such a manner as to be overlapped with the pulse wave displayed on the displaying means.

The above-mentioned object can also be achieved by providing a noncontact type tonometer comprising a pulse wave detecting means, and a calculating means for finding at least one of the maximum eye pressure value, minimum eye pressure value and average eye pressure of an eye-to-be-tested through calculation with reference to the relation among the maximum fluctuation width of the pulse wave detected by the pulse wave detecting means and the pulse wave fluctuating quantity at the time point when the measurement of the eye pressure is carried out by the eye pressure measuring portion and the measuring value of the eye pressure.

According to the above-mentioned constitution of the present invention, at least one of the maximum eye pressure value, minimum eye pressure value and average eye pressure value can be found by the calculating means.

EMBODIMENT

The embodiment of a noncontact type tonometer according to the present invention will be described with reference to FIGS. 1 through 5.

Figure 1:
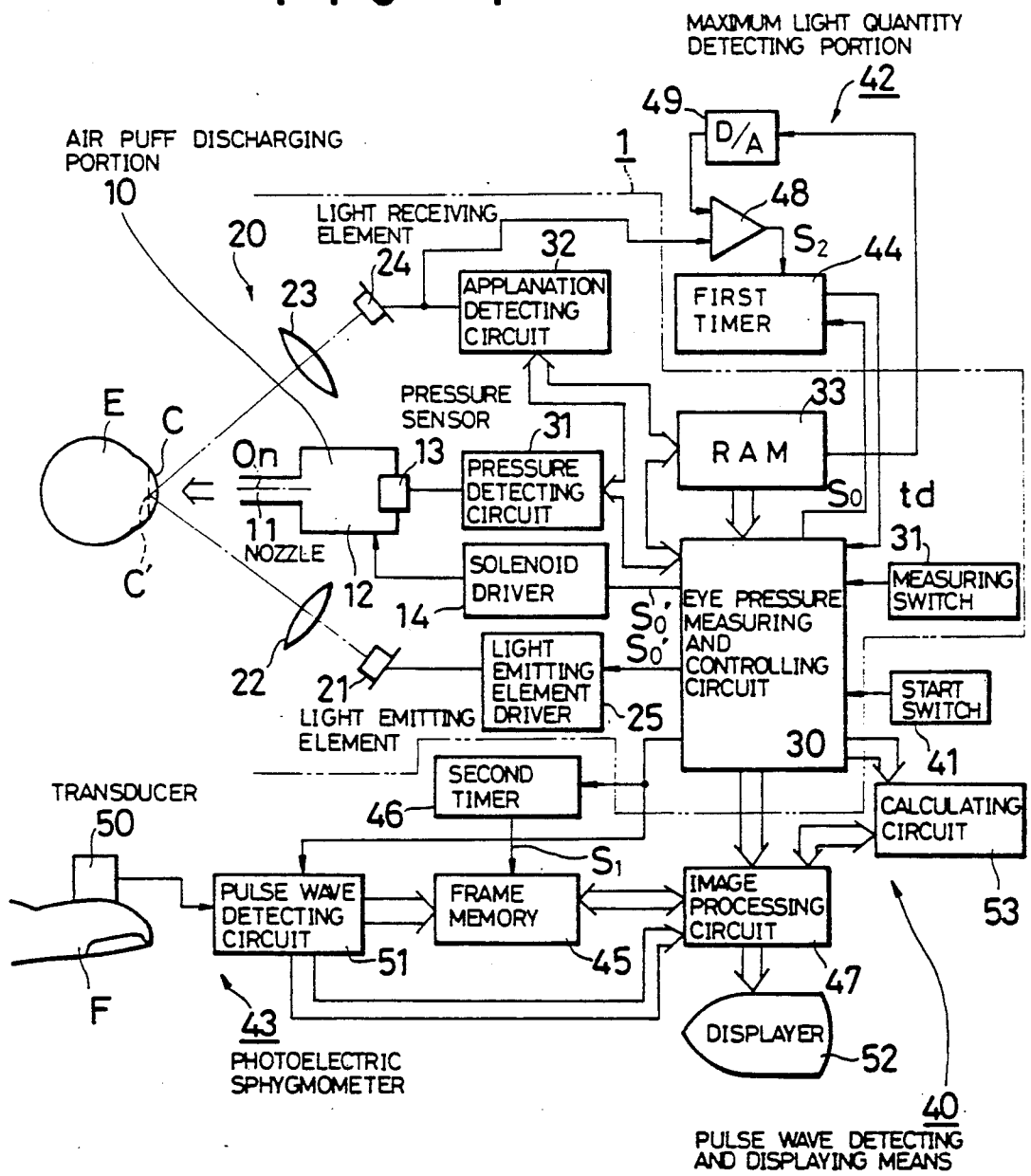
FIG. 1 is a block diagram showing the constitution of an important portion of a noncontact type tonometer according to the present invention.

In FIG. 1, 1 denotes an eye pressure measuring portion. The constitution of this eye pressure measuring portion 1 is described in detail in Patent Application No. Sho 59-242279 (Patent Application Early Laid-open Publication No. Sho 61- 122839) which has been filed by the present applicant prior to this application. The eye pressure measuring portion 1 has an air puff discharging portion 10 for discharging a fluid such as air toward the cornea C of an eye-to-be-tested E to transfigure the cornea C and an eye pressure measuring/controlling circuit 30. The air puff discharging portion 10 has a nozzle 11, an air chamber 12, and a piston and a cylinder not illustrated. The air chamber 12 is provided with a pressure sensor 13. The nozzle 11 is adapted to discharge air. The pressure sensor 13 is adapted to measure air pressure within the air chamber 12. The cylinder is slidably fitted therein with a piston. The piston is driven by a solenoid not illustrated, and the solenoid is magnetized by a solenoid driver 14. When the piston is driven, air within the cylinder is transferred into the air chamber 12 under pressure and air within the air chamber 12 is discharged toward an eye-to-be-tested E from the nozzle 11.

A corneal transfiguration detecting system 20 comprises a pair of optical systems which are symmetrically disposed at the both sides of the axis $O_n$ of the nozzle 11. In FIG. 1, the schematic constitution of the pair of optical systems are illustrated, wherein 21 denotes a light emitting element, 22 denotes a projecting lens, 23 denotes an imaging lens, and 24 denotes a light receiving element. The light emitting element 21 is driven by a light emitting element driver 25. Light emitted by the light emitting element 21 is made into parallel pencil of rays by the projecting lens 22 and projected toward a cornea C from a diagonal direction. The light reflected by the cornea C is condensed by the imaging lens 23 and imaged on a light receiving surface of the light receiving element 24. The light receiving surface of the light receiving element 24 is disposed at the focal position of the imaging lens 23.

The eye pressure measuring and controlling circuit 30 is connected with a measurement start switch 31. The measurement start switch 31 is adapted to move the eye pressure and controlling circuit 30 to an eye pressure measuring step. The eye pressure measuring and controlling circuit 30 has such a function as to actuate the light emitting driver 25 in accordance with a measuring start command $S_0'$ of the measurement start switch 31 and to actuate the solenoid driver 14. When the solenoid driver 14 is actuated, the piston is actuated, pressure within the air chamber 12 is increased, the pressure is successively detected by the pressure sensor 13, and the detected output is input into the pressure detecting circuit 31 as a detecting pressure data. This detecting pressure data corresponds to the air pressure as a fluid discharged from the nozzle 11. On the other hand, a cornea reflecting light quantity L from the cornea C is successively detected by the light receiving element 24 in the process where the cornea C is transfigured by a predetermined quantity, and the reflecting light quantity signal based on the cornea reflecting light quantity L is input into an applanation detecting circuit 32. The applanation detecting circuit 32 has such a function as to convert the reflecting light quantity signal to a reflecting light quantity as a digital signal.

Figure 2:
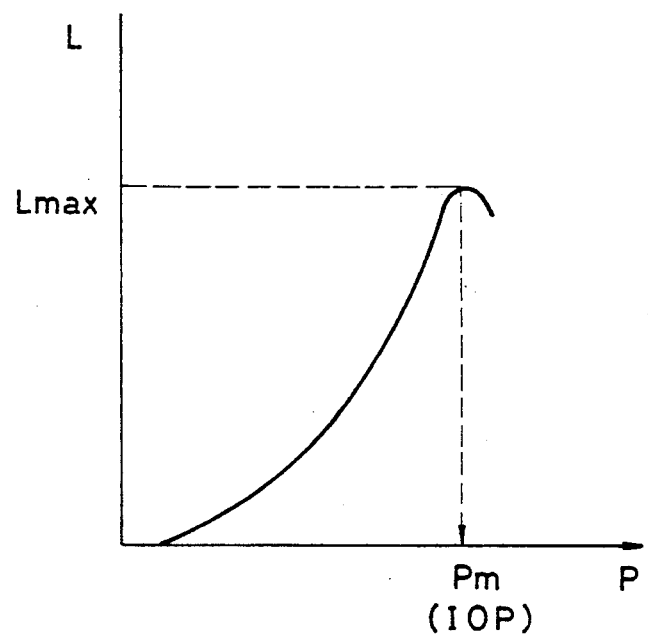
FIG. 2 is a graph for explaining the relation between a detection pressure P and a cornea reflecting light quantity L which have been detected in the process of the corneal transfiguration when an eye pressure is measured.

The pressure detecting circuit 31 has such a function as to cause RAM 33 to memorize the cornea reflecting light quantity data detected by the applanation detecting circuit 32 every time the detecting pressure data from the pressure sensor 31 is increased by a predetermined unit pressure. Therefore, the RAM 33 is renewed the address in such a manner as to graduate the predetermined unit pressure every time the detecting pressure data of the pressure detecting circuit 31 is increased by the predetermined unit pressure, and the reflecting light quantity data from the applanation detecting circuit 32 is stored in each address. By this, a pressure-light quantity function, in which, as shown in FIG. 2, a detecting pressure P is taken on the horizontal axis and a corneal reflecting light quantity L is taken on the vertical axis, is stored in the RAM 33. The eye pressure measuring portion of the eye pressure measuring and controlling circuit 30 finds a detecting pressure data $P_m$ corresponding to the cornea reflecting light quantity L of maximum Lmax in which the cornea C is made into applanation (see the reference character C' of FIG. 1) from the pressure-light quantity function stored in the RAM 33, and finds an eye pressure IOP of the eye-to-be-tested E with reference to the detecting pressure data Pm.

In a noncontact type tonometer according to the present invention, the eye pressure measuring portion 1 is added with a pulse wave detecting and calculating means 40 as will be described hereinafter. This pulse wave detecting and calculating means 40 has a start switch 41, a maximum light quantity detecting portion 42, a known photoelectric sphygmometer 43 as a pulse wave detecting means for detecting the pulse wave of the eye-to-be-tested, a first timer 44, a frame memory 45, a second timer 46, an image processing circuit 47 and a calculating circuit 53. The start switch 41 is connected to the eye pressure measuring and controlling circuit 30. The maximum light quantity detecting portion 42 comprises a comparator 48 and a D/A converter 49. The comparator 48 and the D/A converter 49 are cooperated with each other to detect the time point when a cornea reflecting light quantity L as an analog signal which is directly input from the light receiving element 42 becomes maximum. The photoelectric sphygmometer 43 comprises a transducer 50 and a pulse wave detecting circuit 51 for detecting voltage of the transducer 50 and outputting it as a pulse wave form. The transducer 50 is mounted on, for example, a finger tip F of the person-to-be-tested. The output of the pulse wave detecting circuit 51 is input into the frame memory 45 and an image processing circuit as will be described. The pulse wave form is stored in the frame memory 45. The first timer 44 has such a function as to count the time point when the cornea reflecting light quantity L of the applanation detecting circuit 32 becomes maximum Lmax. The second timer 46 has such a function as to control the memory renewal of the frame memory 45. The image processing circuit 47 has such a function as to compose the images of an eye pressure measuring value IOP output from the eye pressure measuring and controlling circuit 30 and a pulse wave form PW output from the frame memory 46 or the pulse wave detecting circuit 51. The output of the composed image is input into a displayer 52 as displaying means for displaying the pulse wave form detected by the photoelectric sphygmometer 43 to display the composed image. As the displayer 52, a CRT is used for example. The detail of the composed image will be described afterward.

Prior to the measurement of an eye pressure, the control unit of the eye pressure measuring and controlling circuit 30 simultaneously starts the second timer 46 and the pulse wave detecting circuit 51. Then, the transducer 50 photoelectrically detects the change regarding the pulse wave such as light transmittance and light reflectivity due to flow-in/flow-out of blood at the finger tip F and outputs its as a voltage change.

The output of the voltage change is input in the pulse wave detecting circuit 51. The pulse wave detecting circuit 51 outputs a signal corresponding to the pulse wave form PW to the frame memory 45 and the image processing circuit 47 based on the voltage change. The image processing circuit 47 has the displaying portion 52a of the displayer 52 display the pulse wave form PW according to the signal output of the pulse wave detecting circuit 51 (see FIG. 5). On the other hand, the frame memory 45 memorizes a signal corresponding to the pulse wave form PW.

The second timer 46 outputs a command signal $S_1$ to the frame memory 45 every time it counts a predetermined time Tm (see FIG. 4) from a command time point $t_0$ by the start switch 41. In this embodiment, taking into consideration a case where the number of pulse of a person is small, 50 times/min., for example, the predetermined time Tm is set to 2.4 sec. corresponding to two times the pulse number. The pulse wave form PW stored in the frame memory 45 is renewed every time a renewal command signal $S_1$ is renewed.

Next, the measuring switch 31 is put on. Then, the eye pressure measuring and controlling circuit 50 goes to an eye pressure measuring step. The first timer 44 starts a time-counting according to a command $S_0$ of the control unit of the eye pressure measuring and controlling circuit 30 based on the putting-on operation of the measuring switch 31. The light receiving element 24 also outputs a reflecting light signal as the analog signal during the operation of the eye pressure measuring step to one input terminal of the comparator 48. The comparator 48 constitutes a part of the maximum light quantity detecting portion 42. An analog signal of the D/A converter 49 is input in the other input terminal of the comparator 48. The D/A converter 49 converts a digital signal output from the RAM 33 to an analog signal. The RAM 33 outputs a reflecting light quantity data, as a digital signal, stored in the address immediately before a predetermined unit pressure is increased by the control unit of the eye pressure measuring and controlling unit every time the detecting pressure data is increased by the predetermined unit pressure to the D/A converter 49.

Figure 3:
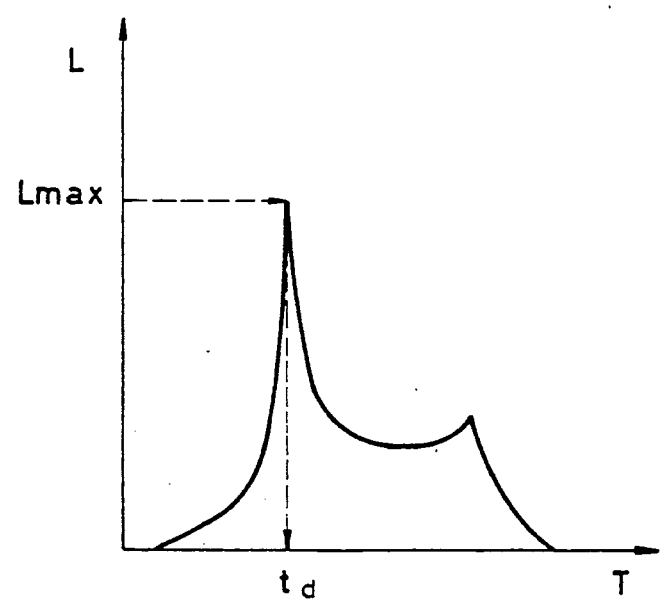
FIG. 3 is a graph for explaining the relation between the cornea reflecting light quantity and the time when the cornea is transfigured.

The comparator 48 compares the largeness of the reflecting light quantity signal of the light receiving element 24 with the largeness of the signal from the D/A converter 49 analogwise in light quantity and outputs a stop signal $S_2$ to the first timer 44 when the largeness of the reflecting light quantity signal input from the light receiving element 24 becomes smaller than that of the reflecting light quantity data of the RAM 33 input through the D/A converter 49. This means that it detects the maximum Lmax of the cornea reflecting light quantity L. The first timer 44 counts the time point when the reflecting light quantity signal becomes maximum and outputs the counted time td to the eye pressure measuring and controlling circuit 30 as a time-counting data. By this, there can be obtained the counted time td at the time point when the cornea reflecting light quantity L becomes the maximum Lmax as shown in FIG. 3.

When the time counting data as the counted time td is input from the first timer 44, the eye pressure measuring and controlling circuit 30 controls the image processing circuit 47 as such that a signal corresponding to the pulse wave form PW of the pulse wave detecting circuit 45 is prohibited from being input into the image processing circuit 47 and a signal corresponding to the pulse wave form PW of the frame memory 45 is input into the image processing circuit 47. By this, the pulse wave forms PW of two adjacent front and after waves including the time point when the eye pressure IOP is measured are stationarily displayed on the pulse wave displaying portion 52a of the displayer 52.

When attention is paid to the pulse wave of the finger tip F and the pulse wave of the eye-to-be-tested E here, the phase of the pulse wave at the finger tip F is not necessarily coincident with the phase of the pulse wave at the eye-to-be-tested E. In general, there can be considered that a propagation delay time $\Delta t$ is present between the pulse wave form PW at the finger tip F and the pulse wave form PW at the eye-to-be-tested E. The phase of the pulse wave form PW at the finger tip F is advanced than the phase of the pulse wave form at the eye-to-be-tested E. Therefore, the eye pressure measuring time $t_p$ is found in such a manner as that the propagation delay time $\Delta t$ is set beforehand and then this propagation delay time $\Delta t$ is deducted from the counted time td (cornea applanation time) td. (see FIG. 4). This calculation is carried out by the calculating circuit 53 connected to the eye pressure measuring and controlling circuit 30. The cycle of the pulse wave form PW is from approximately 500 m sec to 1000 m sec, whereas the eye pressure measuring time by the eye pressure measuring portion 1 is 10 m sec or less. Accordingly, an individual difference of the propagation delay time $\Delta t$ can be practically disregarded.

The eye pressure measuring and controlling circuit 30 obtains a peak value (the pulse wave fluctuating position at the eye pressure measuring time $t_p$) CP of the pulse wave form PW at the eye pressure measuring time $t_p$ by having the obtained eye pressure measuring time $t_p$ and the time axis of the pulse wave form PW stored in the frame memory 45 correspond with each other. And, the eye pressure measuring and controlling circuit 30 controls the image processing circuit 47 as such that the displayer 52 displays a target mark I showing the phase place of the pulse wave where the eye pressure measurement is carried out or not overlapped with a place corresponding to the peak value (the pulse wave fluctuating position at the eye pressure measuring time $t_p$) CP. That is, the eye pressure measuring and controlling circuit 30 functions as display controlling means for controlling the image processing circuit 47 so as to have the displayer 52 displays the target mark I showing the phase place of the pulse wave where the eye pressure measurement is carried out in such a manner as to overlap with the pulse wave form PW displayed on the displaying means together with the frame memory 45, the second timer 46, the maximum light quantity detecting portion 42 and the image processing circuit 47.

In this embodiment, an anterior portion image AP and an alignment target image AI obtained both by an anterior portion image observating optical system not shown and an alignment detecting optical system not shown are displayed on the upper half displaying surface of the displayer 52. The details of the constitution of the anterior portion image observing optical system and the alignment detecting optical system are described in Japanese Patent Application No. Sho 60-59994 (Patent Application Early Laid-open Publication No. Sho 61-220625) which was filed by the present applicant.

Figure 4:
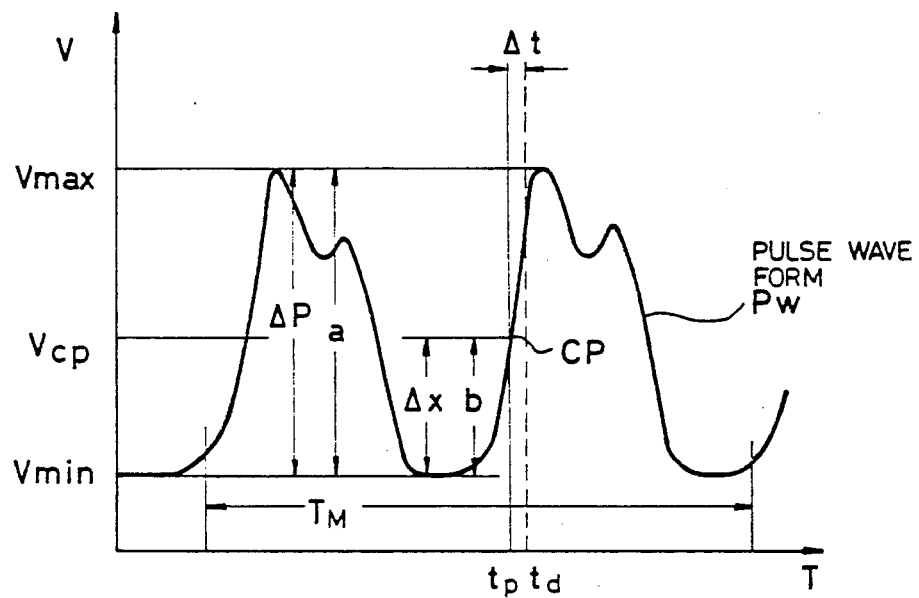
FIG. 4 is an enlarged view of the pulse wave form.

The calculating circuit 53 finds the maximum fluctuation width a of the pulse wave form PW as a difference between the detection voltages Vmax and Vmin based on the data of the pulse wave form PW of the frame memory 45 as shown in FIG. 4. Also, the calculating circuit 53 finds the fluctuating quantity b of the pulse wave form PW at the eye pressure measuring time $t_p$ of the eye pressure measuring value IOP as a difference between the detection voltages Vcp and Vmin at the peak value (the pulse wave fluctuating position) CP.

That is, it is found based on the following formulas.

$$a = Vmax - Vmin \quad (1)$$

$$b = Vcp - Vmin \quad (2)$$

The maximum fluctuation width a corresponds to the maximum eye pressure fluctuation width $\Delta P$ caused by the fluctuation of the pulse wave form PW. The following relation can be obtained between the fluctuating quantity $\Delta x$ of the eye pressure corresponding to the pulse wave form PW and the maximum eye pressure fluctuation width $\Delta P$.

$$\Delta x = \frac{b}{a} \cdot \Delta P \quad (2)$$

Although the pulse wave form PW obtained by the photoelectric sphygmometer 43 shows the fluctuating state of the pulse pressure, it does not show the absolute value of blood pressure.

Therefore, in a noncontact type tonometer according to the present invention, the minimum eye pressure value IOP l of the eye-to-be-tested E and the maximum eye pressure value IOPh and the average eye pressure value $\overline{IOP}$ are found from the measuring eye pressure value $\overline{IOP}$, the maximum fluctuation width a of the pulse wave form PW and the pulse wave fluctuating quantity b based on the formula (2) and the following formulas (3), (4) and (5).

$$IOPh = \overline{IOP} - \Delta x \quad (3)$$
$$= IOP - \frac{b}{a} \cdot \Delta P$$

$$IOPh = IOP + \Delta P \quad (4)$$

$$\overline{IOP} = IOPl + \frac{\Delta P}{2} \quad (5)$$

The formula (4) is naturally valid because the difference between the maximum eye pressure value IOPh and the minimum eye pressure value IOP l means the maximum eye pressure fluctuation width $\Delta P$.

The calculating circuit 53 comprises, for example, a microprocessor, and the calculation of the formulas (1) through (5) is processed by software. The maximum eye pressure fluctuation width $\Delta P$ of the formulas (1) through (5) are found through theory, experiment or experience and is stored in a memory of the calculating circuit 53 beforehand as, for example, 4.0 mmHg. In this embodiment, the measuring eye pressure value IOP is, for example, 16.0 mmHg.

First, in the formula (1)

$$a = Vmax - Vmin \quad (6)$$

and a predetermined unitless number, 128, is alloted to the maximum fluctuation width a. The relation a=128 means that the difference between Vmax and Vmin is equally divided into 128 portions.

Next, the pulse wave fluctuation width b of the eye pressure measuring time $t_p$ of the measuring eye pressure value $\overline{IOP}$ is found from the formula (1)' as a unitless number.

$$b = \frac{Vcp - Vmin}{Vmax - Vmin} \times (128) \quad (7)$$

Vmax, Vmin and Vcp are substituted by actually measured values. For example, suppose that b=60 is obtained.

Then, the following answer is obtained from the formula (3) regarding the minimum eye pressure value IOP l.

$$IOPl = 16.0 - \frac{60}{128} \times 4.0$$
$$= 14.1 \text{ mmHg}$$

The following answer can be obtained from the formula (4) regarding the maximum eye pressure value IOPh.

$$IOPl = 14.1 + 4.0$$
$$= 18.1 \text{ mmHg}$$

Likewise, the following answer can be obtained from the formula (5) regarding the average eye pressure value $\overline{IOP}$.

$$\overline{IOP} = 14.1 + \frac{4.0}{2}$$
$$= 16.1 \text{ mmHg}$$

Figure 5:
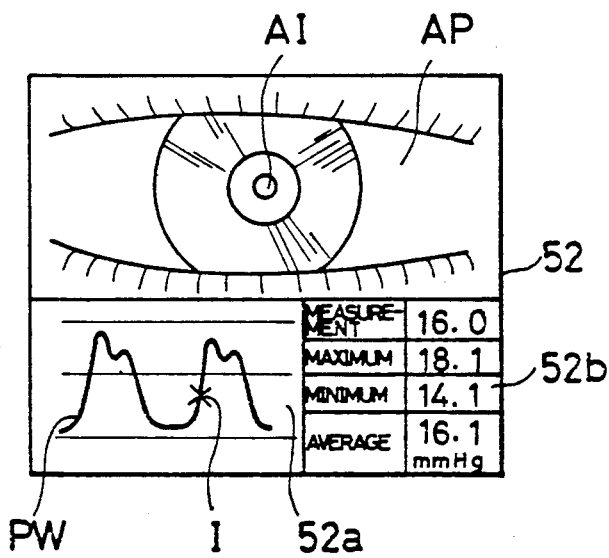
FIG. 5 is an illustration showing one example of items displayed on the displaying device.

IOPh, IOPl and $\overline{IOP}$ as a result of calculation of the calculating circuit 53 are output to the image processing circuit 47. The image processing circuit 47 has the eye pressure displaying portion 52b of the displayer 52 display the expectable maximum eye pressure value IOPh, minimum eye pressure value IOPh and average eye pressure value $\overline{IOP}$ together with the measuring eye pressure value $\overline{IOP}$ as shown in FIG. 5.

In the above embodiment, the pulse wave is detected by using the photoelectric sphygmometer 43. However, the present invention is not limited to this. For example, an impedance plethysomgraph for measuring the change of capacity based on the change of blood flow as a change of impedance may be used. In the embodiment, the transducer 50 of the photoelectric sphygmometer 43 is mounted on the finger tip F of a person-to-be-tested. However, the transducer 50 may be mounted on a forehead receiver of a frame of the noncontact type tonometer so that the forehead or the temple of the person-to-be-tested is abutted against it. In this case, the propagation delay time $\Delta t$ between the pulse wave form detected by the photoelectric sphygmometer 43 and the pulse wave form within the eye ball can be practically disregarded, and the correction of the eye pressure measuring time $t_p$ based on the propagation delay time $\Delta t$ can be omitted.

Furthermore, in this embodiment, as the constitution of the eye pressure measuring portion 1, one which uses the light quantity-pressure relation is employed. However, for example, a form which uses the light quantity-time function as disclosed in Japanese Patent Publication No. Sho 54-38437 may be employed. In this case, the output of the applanation detecting system outputs the time at the time point when the cornea reflecting light quantity L becomes maximum Lmax as a applanation detecting data. Accordingly, the first timer 44 and the maximum light quantity detecting portion 42 can be omitted.

A noncontact type tonometer according to the present invention is constituted as such that the pulse wave of a person-to-be-tested is displayed and in addition, the time point when the eye pressure is measured is displayed in such a manner as to overlap with the displaying pulse wave. Accordingly, a person who carries out the measurement can visually recognize the dynamic form of the pulse wave. In addition, he can intuitively recognize the phase place of the pulse wave fluctuation where the eye pressure value is measured. Therefore, he can recognize the measuring eye pressure value as a correlation with the pulse wave fluctuation. Therefore, a meaning can be given to the measuring eye pressure value and an increased reliability thereof can be expected. If it is designed as such that at least one of the maximum eye pressure value, minimum eye pressure value and average eye pressure value of the eye-be-tested can be found in addition to the measuring eye pressure value, the reliability of the eye pressure measurement can be more increased than the prior art.

Furthermore, the alignment operation of the tonometer can be performed more easily compared with the conventional tonometer in which the eye pressure is performed in synchronism at the same phase place of the pulse wave based on the pulse wave fluctuation.

We claim:

1. A noncontact type tonometer comprising fluid projecting means for projecting a fluid toward an eye-to-be-tested, eye pressure measuring means for obtaining a measured value of the eye-to-be-tested from a relation between a transfiguring quantity of the eye-to-be-tested and the pressure of the fluid, pulse wave detecting means for detecting a pulse wave of a person-to-be-tested, and calculating means coupled to the pulse wave detecting means and said eye pressure measuring means for determining at least one of the maximum eye pressure value, minimum eye pressure value and average eye pressure value of the eye-to-be-tested through calculation with reference to the maximum fluctuation width of the pulse wave detected by the pulse wave detecting means, the pulse wave fluctuating quantity at the time point when the measurement of the eye pressure is carried out by the eye pressure measuring means, and the measured value of the eye pressure.

2. A noncontact type tonometer according to claim 1 and further comprising:
    displaying means connected to said pulse wave detecting means for displaying the pulse wave.

3. A noncontact type tonometer comprising means for projecting fluid toward an eye-to-be-tested and measuring an eye pressure of the eye-to-be-tested from a relation between a transfiguring quantity of the eye-to-be-tested and the pressure of the fluid,
    pulse wave detecting means for detecting a pulse wave of a person-to-be-tested, displaying means for displaying a pulse wave form detected by said pulse wave detecting means, and overlap display controlling means for displaying the time point when the measurement of the eye pressure is carried out in such a manner as to overlap with the pulse wave form displayed on said displaying means.

* * * * *